US00PP37287P3

(12) United States Plant Patent
Schoone

(10) Patent No.: US PP37,287 P3
(45) Date of Patent: Feb. 24, 2026

(54) ***PHALAENOPSIS* PLANT NAMED 'Coronado'**

(50) Latin Name: *Phalaenopsis hybrida*
Varietal Denomination: Coronado

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 19/243,678

(22) Filed: Jun. 19, 2025

(65) Prior Publication Data

US 2025/0393487 P1 Dec. 25, 2025

Related U.S. Application Data

(60) Provisional application No. 63/662,415, filed on Jun. 20, 2024.

(51) Int. Cl.
*A01H 5/02* (2018.01)
*A01H 6/62* (2018.01)

(52) U.S. Cl.
USPC ..... Plt./311
CPC ..... *A01H 6/62* (2018.05); *A01H 5/02* (2013.01)

(58) Field of Classification Search
USPC ..... Plt./311
CPC ..... A01H 5/02; A01H 5/00; A01H 6/62
See application file for complete search history.

*Primary Examiner* — June Hwu
(74) *Attorney, Agent, or Firm* — C. Anne Whealy

(57) ABSTRACT

A new and distinct cultivar of *Phalaenopsis* plant named 'Coronado', characterized by its upright plant habit; relatively strong flowering stems; healthy and sturdy leaves; freely flowering habit with typically two inflorescences developing per plant, each inflorescence with numerous flowers; flower petals and sepals that are reddish purple in color; and good postproduction longevity.

2 Drawing Sheets

Figure 1:
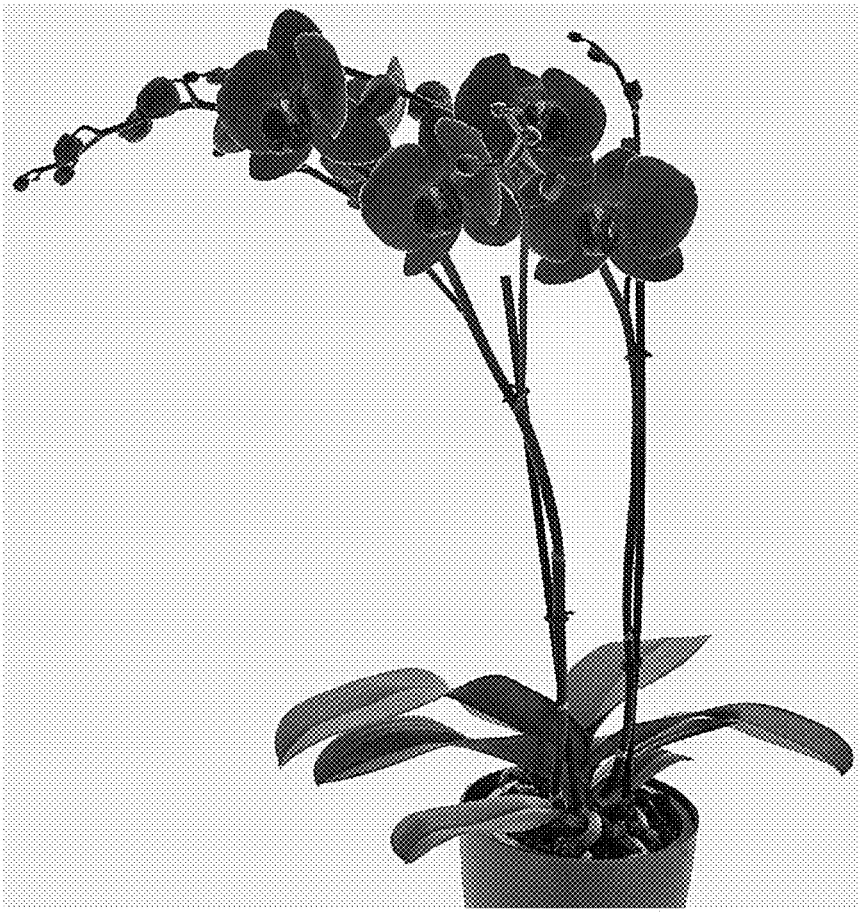

Botanical designation: *Phalaenopsis hybrida.*
Cultivar denomination: 'CORONADO'.

A European Community Plant Breeder's Rights application for the instant plant was filed by the Applicant/Assignee, Floricultura B.V. of Heemskerk, The Netherlands on Jun. 7, 2024, application number 2024/1299. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'Coronado'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in August 2014 in Assendelft, The Netherlands of a proprietary selection of *Phalaenopsis hybrida* identified as code number MP1762, not patented, as the female, or seed, parent with a proprietary selection of *Phalaenopsis hybrida* identified as code number B3024, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in November 2020.

Asexual reproduction of the new *Phalaenopsis* plant by in vitro meristem propagation in a controlled environment in Assendelft, The Netherlands since November 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Coronado'. These characteristics in combination distinguish 'Coronado' as a new and distinct *Phalaenopsis* plant:

1. Upright plant habit.
2. Relatively strong flowering stems.
3. Healthy and sturdy leaves.
4. Freely flowering habit with typically two inflorescences developing per plant, each inflorescence with numerous flowers.
5. Flower petals and sepals that are reddish purple color.
6. Good postproduction longevity.

Plants of the new *Phalaenopsis* can be compared to plants of the female parent selection. Plants of the new *Phalaenopsis* differ primarily from plants of the female parent selection in flower color as flower petals of plants of the new *Phalaenopsis* do not have any spots whereas flower petals of plants of the female parent selection are spotted. In addition, the lateral lobe of the flower labella of plants of the new *Phalaenopsis* are dark reddish purple in color whereas the lateral lobe of the flower labella of plants of the female parent selection are purplish red and creamy white in color.

Plants of the new *Phalaenopsis* can be compared to plants of the male parent selection. Plants of the new *Phalaenopsis* differ primarily from plants of the male parent selection in the following characteristics:

1. Plants of the new *Phalaenopsis* are not as tall as plants of the male parent selection.
2. Flower petals of plants of the new *Phalaenopsis* are not as "free" as flower petals of plants of the male parent selection.
3. Flowers of plants of the new *Phalaenopsis* are concave in lateral view whereas flowers of plants of the male parent selection are convex in lateral view.

Plants of the new *Phalaenopsis* can be compared to plants of *Phalaenopsis hybrida* 'Vivaldi', not patented. In side-by-side comparisons, plants of the new *Phalaenopsis* differ primarily from plants of 'Vivaldi' in the following characteristics:

1. Leaves of plants of the new *Phalaenopsis* are longer than leaves of plants of 'Vivaldi'.
2. Cirrhose apices of the flower labella of plants of the new *Phalaenopsis* are longer than the cirrhose apices of the flower labella of plants of 'Vivaldi'.
3. Peduncles of plants of the new *Phalaenopsis* are strongly tinged with anthocyanin whereas peduncles of plants of 'Vivaldi' are slightly tinged with anthocyanin.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Coronado' grown in a container.

Figure 2:
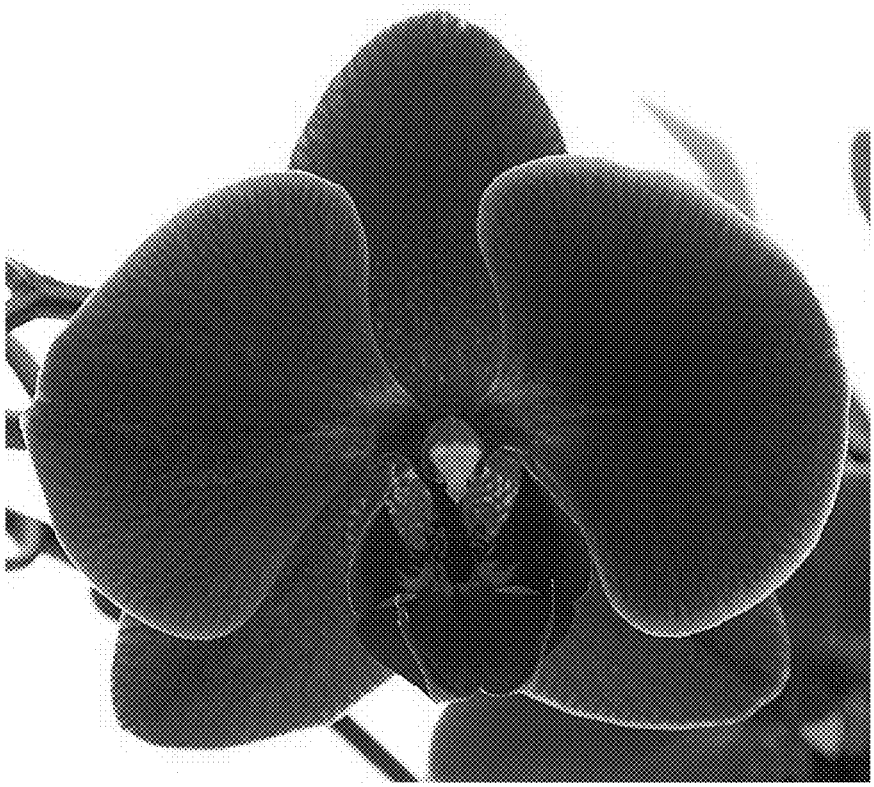

The photograph on the second sheet (FIG. 2) is a close-up view of a typical flower of 'Coronado'.

DETAILED BOTANICAL DESCRIPTION

The aforementioned photographs and following observations and measurements describe plants grown during the summer in 11-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Coronado'.

Parentage:

*Female, or seed, parent*.—Proprietary selection of *Phalaenopsis hybrida* identified as code number MP1762, not patented.

*Male, or pollen, parent*.—Proprietary selection of *Phalaenopsis hybrida* identified as code number B3024, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thin, fibrous; typically light yellowish white in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit with typically two inflorescences developing per plant, each inflorescence with numerous flowers; monopodial; relatively moderately vigorous growth habit and moderate growth rate.

*Plant height, substrate level to top of foliar plane*.—About 11.3 cm.

*Plant height, substrate level to top of floral plane*.—About 43.5 cm.

*Plant diameter or spread*.—About 32.1 cm.

Leaf description:

*Arrangement and quantity*.—Distichous, simple; sessile; about six to seven fully-developed leaves per plant.

*Length*.—About 17.7 cm.

*Width*.—About 6.4 cm.

*Aspect*.—Outwardly arching.

*Shape*.—Obovate-oblong to narrowly obovate-oblong; slightly carinate.

*Apex*.—Unequal broadly acute.

*Base*.—Sheathing. Sheath length: About 1.6 cm. Sheath width: About 1.1 cm. Sheath color, upper and lower surfaces: Close to a blend of 143B and 143C and moderately to strongly tinged with close to 197C.

*Margin*.—Entire.

*Texture and luster, upper surface*.—Smooth, glabrous; slightly glossy.

*Texture and luster, lower surface*.—Smooth, glabrous; moderately glossy.

*Venation pattern*.—Camptodromous.

*Color*.—Developing leaves, upper surface: Close to NN137A; towards the base, close to 200B with narrow marginal edges, close to 200B. Developing leaves, lower surface: Close to 146B strongly tinged with close to N186C with narrow marginal edges, close to a blend of N186C and 200A. Fully expanded leaves, upper surface: Close to 137B; narrow marginal edges, close to 197A and 197B; venation, close to 147A. Fully expanded leaves, lower surface: Close to 146B slightly tinged with close to N186C; narrow marginal edges, close to a blend of N186C and 200A; venation, close to a blend of N186C and 200A.

Inflorescence description:

*Appearance and flowering habit*.—Showy zygomorphic flowers arranged on axillary simple or branched racemes; typically two inflorescences develop per plant; each inflorescence with about 15 flowers;

flowers face mostly outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity and postproduction longevity*.—Long flowering period and good postproduction longevity, individual flowers maintain good substance for about eleven weeks on the plant; flowers not persistent.

*Inflorescence length* (*lowermost flower to inflorescence apex*).—About 27.6 cm.

*Inflorescence width*.—About 15.3 cm.

*Flower buds*.—Height: About 1.9 cm. Diameter: About 1.4 cm by 1.6 cm. Shape: Broadly ovate. Color: Close to 183B tinged with close to 187B; towards the base, tinged with close to 152B.

*Flower size*.—About 7.2 cm (vertical) by 8.1 cm (horizontal).

*Flower depth*.—About 3.2 cm.

*Petals, quantity and arrangement*.—Three, two lateral petals and one center petal transformed into a labellum.

*Lateral petals*.—Length: About 3.7 cm. Width: About 4.7 cm. Shape: Broadly reniform; not fused. Apex: Obtuse; occasionally shallowly retuse. Margin: Entire. Texture and luster, upper and lower surfaces: Smooth, glabrous; velvety; matte. Color: When opening, upper surface: Close to a blend of 72A and NN78A; towards the margins and apex, close to NN78A; narrow marginal edges, close to 75A; at the base, marbling, close to 75A; marginal venation, close to N79C. When opening, lower surface: Close to N78A and NN78B; narrow marginal edges, close to 75A; at the base, strongly tinged with close to N187D; venation, close to N79C. Fully opened, upper surface: Close to NN78A; towards the margins and apex, close to 72B; narrow marginal edges, close to 75C; at the base, marbling, close to 76B; marginal venation, close to N78A; colors do not change with subsequent development. Fully opened, lower surface: Close to N78B and NN78C; narrow marginal edges, close to 75C; at the base, slightly tinged with close to N187D; venation, close to N78A; colors do not change with subsequent development.

*Labella*.—Appearance: Three-parted with two lateral lobes and a central lobe. Length, lateral lobes: About 1.8 cm. Width, lateral lobes: About 1.4 cm. Length, central lobe: About 2 cm. Width, central lobe: About 0.7 cm to 2 cm. Shape, lateral lobes: Obovate. Shape, central lobe: Ovate-rhomboidal with an elongated apex. Apex, lateral lobes: Obtuse. Apex, central lobe: Cleft with two cirrhose apices curled upwards and backwards. Margins, lateral and central lobes: Entire. Texture and luster, lateral and central lobes, upper and lower surfaces: Smooth, glabrous, velvety; matte. Callosities: Located at the base of the labellum and attachment point of the lateral petals; about 3.5 mm in length, about 5 mm in width and about 5 mm in height. Color, lateral lobes: When opening, upper surface: Close to N186D; narrow marginal edges, close to N78A; at the base, stripes and blotches, close to 13C and 155A. When opening, lower surface: Close to N186D; towards the margins and apex, close to N78A; at the base, sparse stripes and blotches, close to 13C and 155A. Fully opened, upper surface: Close to N186D; narrow marginal edges, close to N78A; at the base, stripes and blotches, close to 13C and 155A. Fully opened, lower surface: Close to N186D; towards the margins and apex, close to N78A; at the base, sparse stripes and blotches, close to 155A. Color, central lobe: When opening and fully opened, upper surface: Close to N186D; radial stripes, close to 15D; cirrhose apices, close to N186D. When opening and fully opened, lower surface: Close to N186D, N78B and N78C; at the base, close to 156D with blotches, close to 187C. Color, callosities: When developing: Close to 4C; towards the apex, close to 12A; densely dotted and blotched with close to 183B. Fully developed: Close to 4C; towards the apex, close to 13A; densely dotted and blotched with close to 184A.

*Sepals*.—Quantity and arrangement: Three, one upper dorsal sepal and two lower lateral sepals. Length, dorsal sepal: About 4 cm. Width, dorsal sepal: About 3.1 cm. Length, lateral sepals: About 4 cm. Width, lateral sepals: About 2.7 cm. Shape, dorsal sepal: Ovate to elliptic. Shape, lateral sepals: Ovate. Apex, dorsal sepal: Minutely acute. Apex, lateral sepals: Narrowly obtuse. Base, dorsal and lateral sepals: Cuneate. Margins, dorsal and lateral sepals: Entire. Texture and luster, dorsal and lateral sepals, upper and lower surfaces: Smooth, glabrous; moderately velvety; matte. Color, dorsal sepal: When opening, upper surface: Close to 72A; towards the apex and margins, close to a blend of 72B and NN78B; narrow marginal edges, close to 76A; marginal venation, close to N79C; proximal ⅓ of the sepal with sparse fine dots, close to 76A and 76B. When opening, lower surface: Close to 71A and 71B; towards the apex and margins, close to 72B; narrow marginal edges, close to 76A; base tinged with close to 197C; marginal venation, close to N79C. Fully opened, upper surface: Close to NN78A; towards the apex and margins, close to a blend of 72B and NN78B; narrow marginal edges, close to 76A; marginal venation, close to N78A; proximal ⅓ of the sepal with sparse fine dots, close to 76A and 76B; colors do not change with subsequent development. Fully opened, lower surface: Close to N78B; towards the apex and margins, close to N78A; narrow marginal edges, close to 76A; base tinged with close to 195A; marginal venation, close to NN78A; colors do not change with subsequent development. Color, lateral sepals: When opening, upper surface: Distally, close to a blend of N72A and NN78A and towards the margins, close to 72B; proximally, close to 71A with dots, close to 151D, at the base; venation, close to N79C. When opening, lower surface: Close to 72B; proximally, strongly tinged with close to 182C; venation, close to N79C. Fully opened, upper surface: Distally, close to NN78A and towards the margins, close to NN78B with marginal venation, close to N78A; proximally, close to 71A and towards the margins, close to 72B, with marginal venation, close to N79C and at the base, dots, close to 150D; colors do not change with subsequent development. Fully opened, lower surface: Distally, close to N78C and towards the margins, close to N78B; proximally, close to NN78B and NN78C and towards the apex and margins, close to N78A; main vein, close to NN78A and lateral venation, close to N78A; colors do not change with subsequent development.

*Peduncles*.—Length: About 53.3 cm. Diameter: About 5.5 mm. Strength: Strong. Aspect: Upright to outwardly arching. Texture and luster: Smooth, glabrous; matte. Color: Close to 200A moderately covered with fine dots, close to 147B.

*Pedicels*.—Length: About 3.4 cm. Diameter: About 3 mm. Strength: Moderately strong. Aspect: About 80° from peduncle axis. Texture and luster: Smooth, glabrous; matte. Color: Close to a blend of N77B and 183B; distal end, close to 75D; proximal end, close to 187B.

*Reproductive organs*.—Androecium: Column length: About 9 mm. Column width: About 5.5 mm. Column color: Close to NN78A. Pollinia quantity: Two. Pollinia diameter (per two pollinia): About 2.5 mm. Pollinia color: Close to 24A. Gynoecium: Stigma length: About 4 mm. Stigma width: About 4.5 mm. Stigma shape: Reniform. Stigma color: Close to N155A. Ovary length: About 7 mm. Ovary diameter: About 1 mm. Ovary color: Close to 149B. Seeds and fruits: To date, seed and fruit development have not been observed on plants of the new *Phalaenopsis*.

Pathogen & pest resistance:

To date, plants of the new *Phalaenopsis* have not been shown to be resistant to pathogens and pests common to *Phalaenopsis* plants.

Temperature tolerance:

Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Coronado' as herein illustrated and described.

* * * * *